United States Patent
Wu et al.

(10) Patent No.: US 7,789,561 B2
(45) Date of Patent: Sep. 7, 2010

(54) LASER ALIGNED IMAGE GUIDED RADIATION BEAM VERIFICATION APPARATUS

(76) Inventors: Xiaodong Wu, Cyberknife Center of Miami, 7867 N. Kendall Dr., Ste 105, Miami, FL (US) 33156; Ricardo Garcia, Cyberknife Center of Miami, Ste 105, Miami, FL (US) 33156

( * ) Notice: Subject to any disclaimer, the term of this patent is extended or adjusted under 35 U.S.C. 154(b) by 138 days.

(21) Appl. No.: 12/032,628

(22) Filed: Feb. 15, 2008

(65) Prior Publication Data
US 2009/0207977 A1 Aug. 20, 2009

(51) Int. Cl.
*A61B 6/08* (2006.01)
*A61N 5/10* (2006.01)

(52) U.S. Cl. .................... 378/206; 378/65; 378/207
(58) Field of Classification Search ............... 378/62, 378/63, 65, 163, 189, 205–207
See application file for complete search history.

(56) References Cited

U.S. PATENT DOCUMENTS

| | | | |
|---|---|---|---|
| 2,456,096 | A | 12/1948 | Wehmer |
| 4,024,403 | A | 5/1977 | Bernstein et al. |
| 4,158,777 | A | 6/1979 | Hogan |
| 4,210,815 | A | 7/1980 | Riehl |
| 4,293,770 | A | 10/1981 | Vavrek |
| 4,578,806 | A | 3/1986 | Grass et al. |
| 5,138,647 | A | 8/1992 | Nguyen et al. |
| 5,142,559 | A | 8/1992 | Wielopolski et al. |
| 5,517,546 | A * | 5/1996 | Schmidt ............... 378/206 |
| 5,745,545 | A * | 4/1998 | Hughes ................. 378/65 |
| 5,792,146 | A | 8/1998 | Cosman |
| 6,229,873 | B1 * | 5/2001 | Bani-Hashemi et al. ....... 378/63 |
| 6,260,999 | B1 | 7/2001 | Wofford et al. |
| 6,322,249 | B1 | 11/2001 | Wofford et al. |
| 6,407,806 | B2 | 6/2002 | Fujisawa et al. |
| 6,647,092 | B2 | 11/2003 | Eberhard et al. |
| 6,904,125 | B2 * | 6/2005 | Van Dyk et al. ............... 378/65 |
| 7,197,830 | B2 * | 4/2007 | Vaccaro ................. 33/286 |
| 7,198,404 | B2 * | 4/2007 | Navab et al. ............. 378/206 |
| 7,207,715 | B2 | 4/2007 | Yue |
| 7,252,434 | B2 | 8/2007 | Jaradat |
| 7,264,397 | B2 | 9/2007 | Ritter |
| 7,306,368 | B2 | 12/2007 | Isono |
| 7,613,501 | B2 * | 11/2009 | Scherch ............... 600/427 |
| 2002/0080909 | A1 | 6/2002 | Op De Beek et al. |

(Continued)

*Primary Examiner*—Edward J Glick
*Assistant Examiner*—Thomas R Artman
(74) *Attorney, Agent, or Firm*—Pinkert Law Firm, P.A.; Steven Pinkert, Esq

(57) ABSTRACT

A method and apparatus for verifying radiation beam alignment in an image guided stereotactic radiosurgery (SRS) delivery system such as the Cyberknife™. This invention achieves precise verification of radiation beam alignment with a radiation beam detection apparatus mounted on a gimbal assembly. The radiation beam detection apparatus houses an alignment fixture of varying geometric shape, such as a metallic ball or can be an array of radio-opaque markers positioned symmetrically at the gimbal assembly's common rotation center. The radiation detection apparatus comprises a radiation detector such as film and an alignment mirror, which are parallel to each other on opposite sides of the alignment fixture. The radiation detector is used to capture a radiographic image of the alignment fixture and the circular radiation field. The resulting image is analyzed to determine the eccentricity of the radiation field and whether adjustment of node positions is required to eliminate any eccentricity.

8 Claims, 5 Drawing Sheets

U.S. PATENT DOCUMENTS

2003/0206614 A1* 11/2003 Kendrick et al. ............ 378/205
2007/0011176 A1   1/2007 Vishnubhotla
2007/0030959 A1   2/2007 Ritter

* cited by examiner

LASER ALIGNED IMAGE GUIDED RADIATION BEAM VERIFICATION APPARATUS

CROSS-REFERENCE TO RELATED APPLICATIONS

This application claims the benefit of U.S. Provisional Application No. 60/901,553, filed Feb. 15, 2007. The entire disclosure of this prior application is hereby incorporated by reference.

STATEMENT REGARDING FEDERALLY SPONSORED RESEARCH OR DEVELOPMENT

This invention has been created without the sponsorship or funding of any federally sponsored research or development program.

FIELD OF THE INVENTION

The present invention relates generally to the quality assurance of the precision of image-guided robotic radiosurgery systems.

BACKGROUND OF THE INVENTION

Robotic radiosurgery systems, such as CyberKnife™, use a high-precision robotic manipulator, with an image-guided system delivering beams of radiation to the target from multiple predefined beam directions. A robotic arm is used to position a radiation source in order to achieve flexibility in aiming radiation beams. Robot-controlled radiation devices, of which the Cyberknife™ radiosurgery system is one example, contain a linear accelerator (LINAC) mounted on a robotic arm allowing beams of radiation to be directed from any angle. This design is typically referred to as a non-isocentric design. These radiation delivery systems do not usually rotate around a fixed center or axis; therefore, a set of pre-programmed positions is often configured into the system's software to produce repeatable and accurate targeting. A pre-programmed position is defined as a node, and a set of pre-programmed positions (nodes) is defined as a "path".

In order to achieve the accuracy of SRS treatment, each node in a path must be calibrated to a high degree of precision. Most commonly, each node is calibrated so that the radiation beam axis precisely passes through a certain reference point, the alignment center, from a predefined angle. Once initially calibrated (during installation), subsequent verifications are needed to confirm that at each node the radiation beam continues to precisely pass through the alignment center from the predefined angle. The present invention provides an accurate and simple apparatus and method to accomplish the subsequent verification. Prior to the present invention, there is no apparatus or method to accomplish this verification accurately and quickly.

SUMMARY OF THE INVENTION

The present invention is designed to provide the necessary verifications needed to confirm that the radiation beam in an image guided SRS delivery system accurately and precisely passes through the alignment center for optimal results in radiation therapy treatments. The invention achieves verification of the alignment of each node in an image guided SRS system by using the combination of radiographic image guidance and the LINAC's internal laser beam which corresponds with the beam's central axis to precisely align a gimbal based apparatus that indicates alignment. The gimbal based apparatus provides a readout of the quantitative analysis of beam alignment.

BRIEF DESCRIPTION OF THE DRAWINGS

In describing the invention, reference will at times be made to the accompanying drawings in which.

DETAILED DESCRIPTION

Before the subject invention is described further, it is to be understood that the invention is not limited to the particular embodiments of the invention described below, as variations of the particular embodiments may be made and still fall within the scope of the invention. It is also to be understood that the terminology employed is for the purpose of describing particular embodiments, and is not intended to be limiting.

The details of one or more embodiments of the invention are set forth in the accompanying drawings and the description below. Other features, objects, and advantages of the invention will be apparent from the description and drawings, and from the claims. In the following description, numerous specific details are set forth to provide a thorough understanding of the embodiments. One skilled in the art to which this invention belongs will recognize, however, that the techniques described can be practiced without one or more of the specific details, or with other methods, components, materials, etc. In other instances, well known structures, materials or operations are not shown or described in detail to avoid obscuring certain aspects.

In this specification, the singular forms "a," "an" and "the" include plural reference unless the context clearly dictates otherwise. Unless defined otherwise, all technical and scientific terms used herein have the same meaning as commonly understood to one of ordinary skill in the art to which this invention belongs.

Figure 1:
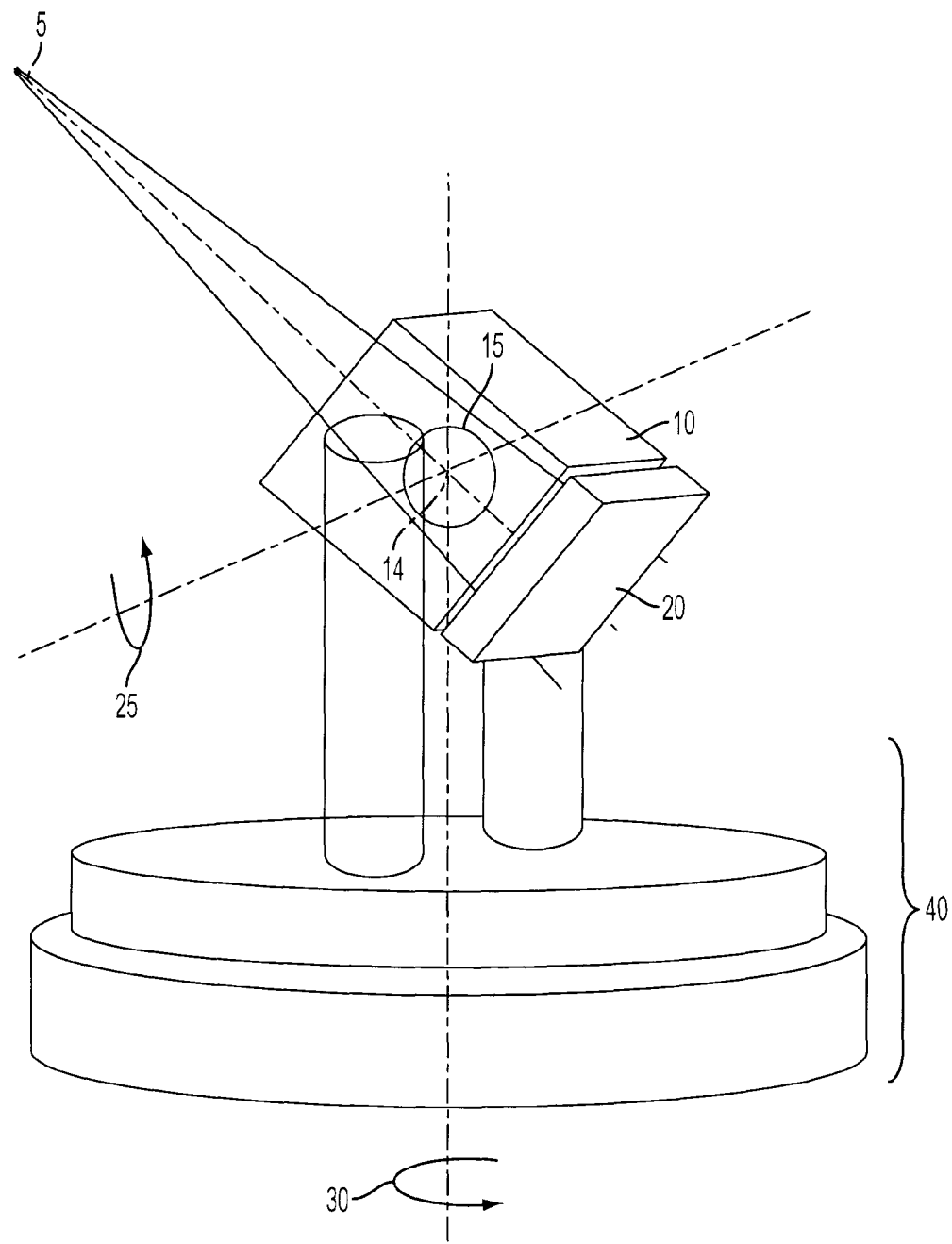
FIG. 1 is a perspective view of the beam detection apparatus of the present invention mounted on a gimbal assembly.

FIG. 1 shows the beam detection apparatus 10 mounted on a gimbal assembly 40. The beam detection apparatus 10 houses an alignment fixture 15. One side of the beam detection apparatus 10 has a radiation detector 20 located behind the alignment fixture 15.

The beam detection apparatus 10 is made of a radio-lucent durable material such as lucite or other suitable material known to one skilled in the art to which this invention belongs. The alignment fixture 15 is made of radio opaque material such as steel or other suitable material known to one skilled in the art to which this invention belongs. A common rotation center of a gimbal is the defined as the point where the two rotation axis of the gimbal intersect and is that point in space that remains stationary when the gimbal is rotated in either axis. The alignment fixture 15 is placed at the gimbal assembly's common rotation center which is to be positioned at the SRS system's alignment center 14. The alignment fixture 15 can take on symmetric geometric shapes such as a square/cube, triangle/pyramid or the like shape in other embodiments of this invention. The alignment fixture 15 can also be an array of radio-opaque markers positioned symmetrically at the gimbal assembly's common rotation center or the like in other embodiments of this invention. In this embodiment of the present invention, the alignment fixture 15 is a metallic ball.

Figure 2:
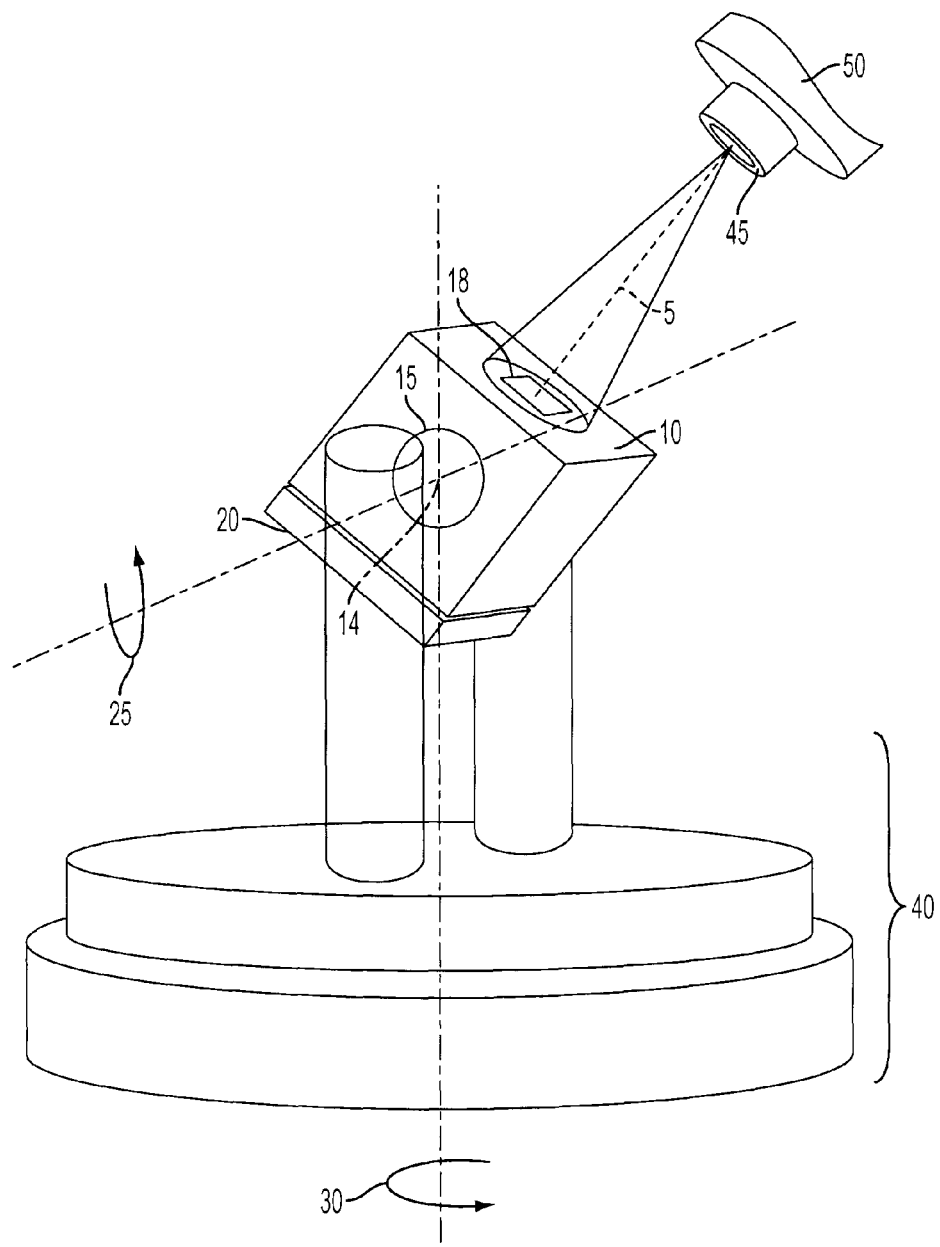
FIG. 2 is another perspective view of the beam detection apparatus of the present invention mounted on a gimbal assembly, showing the alignment mirror component of the apparatus as it used in the invention.

FIG. 2 shows the present invention with the radiation beam detection apparatus 10 mounted on a gimbal assembly 40. A radiation detector 20 such as film is attached to the beam detector apparatus 10. The alignment mirror 18 is shown supported by the beam detector apparatus 10, such that it is parallel to the radiation detector 20. A laser light beam 5 which corresponds to the central axis is shown exiting the LINAC 50 and striking the alignment mirror. The alignment mirror 18 is used to indicate when the radiation detector 20 is perpendicular to the beam central axis. The beam detector apparatus 10 supports the alignment mirror 18 and the radiation detector 20, which are parallel to each other on either side of the alignment fixture 15. The alignment fixture 15 is located at an appropriate distance from the radiation detector 20 in the current embodiment, approximately 2 cm.

The gimbal assembly 40 has two axes of rotation 25 and 30, as shown in FIGS. 1 and 2. This permits the radiation detector 20 to be oriented perpendicular to the central axis at each node. In the current embodiment, markings on the gimbal assembly 40 provide the orientation of the alignment fixture 15 in both axes 25 and 30. Although the current embodiment provides for manually adjusting the gimbal 40, future embodiments will provide motorized adjustment, which will be integrated into the quality assurance software computer program.

Figure 3:
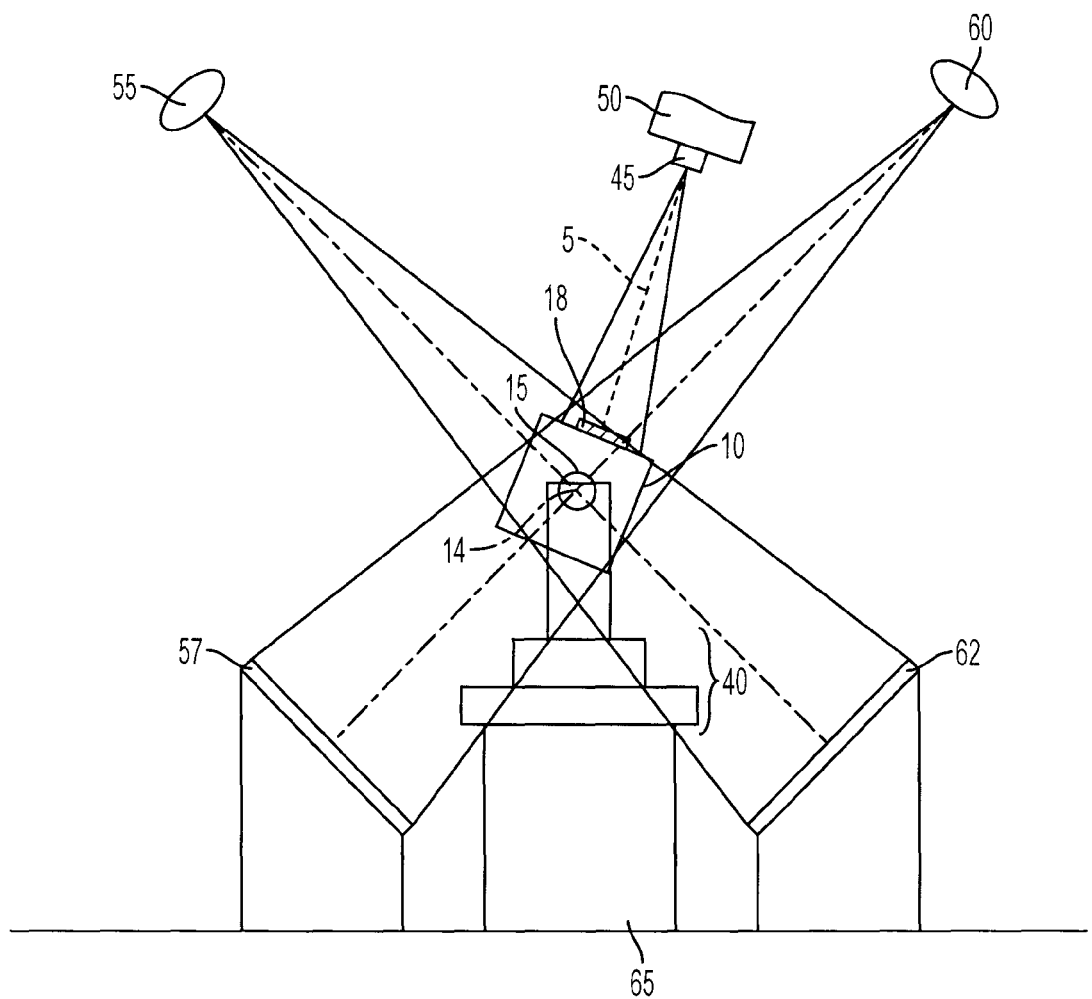
FIG. 3 is a perspective view of the present invention in use with basic components/setup of an image guided SRS system.
Figure 5:
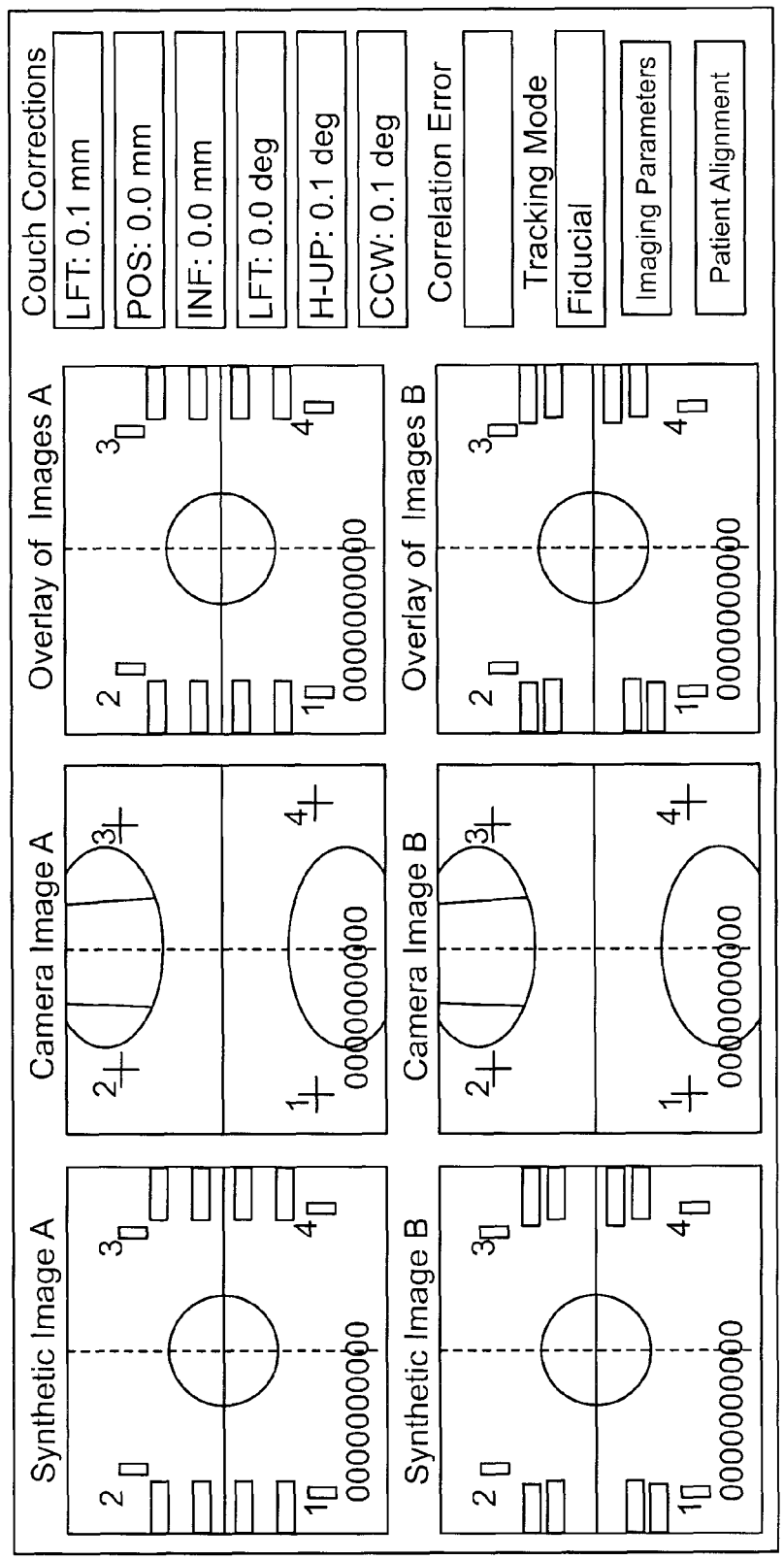
FIG. 5 shows a portion of a computer screen shot of the radiographic image guided alignment results.

FIG. 3 shows the apparatus of the present invention as it is used with an image guided SRS system. The beam detector apparatus 10 mounted on a gimbal assembly 40 is positioned on the treatment table 65 of the SRS system and is flanked on either side by radiographic imaging detectors 57 and 62. Radiographic (x-ray) sources 55 and 60 are positioned above the treatment table 65 at a suitable angle such that the radiation emitted strikes the imaging detectors 57 and 62, aligning perpendicularly at the alignment center 14. This radiographic image guiding system is used to position the gimbal assembly's common rotation center, also the center of the alignment fixture 15, to the SRS system's alignment center. The result of this alignment process is shown in part by FIG. 5. The laser beam 5 that is emitted from the LINAC 45, 50 strikes the alignment mirror 18. The laser beam is reflected to its origin such that the beam central axis is considered perpendicular to the radiation detector 20.

After initial calibration (installation), the orientation of each calibrated node (beam 5) is known. Therefore, the gimbal assembly 40 can be set according to the orientation information of each beam 5 to properly align the film 20 for measurement. As shown in FIGS. 1, 2 and 3, the detector (film) 20 is rigidly mounted in a fixed relationship with the alignment fixture 15 and rotates with the center of the gimbal assembly 40. Either gimbal angle 25 or 30 may be adjusted to rotate and position the film 20 such that it is perpendicular to the axis of the known orientation of the calibrated node (beam). In one embodiment, the process can be fully automated, allowing interfacing between the image guided SRS system and software-controlled stepping motors to align the film 20 with a node (beam) before exposure. This method is carried out for each node.

Figure 4:
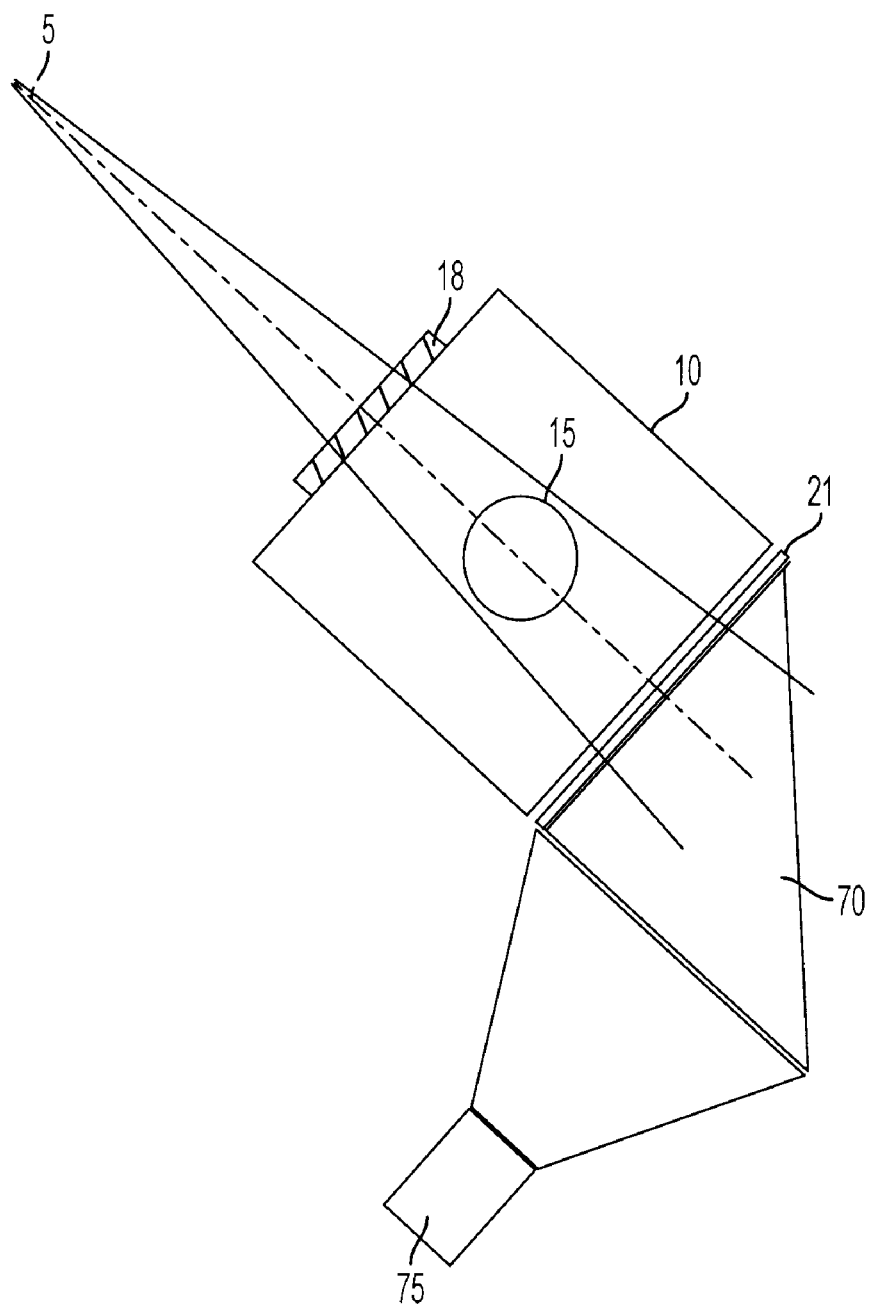
FIG. 4 cross sectional view of one embodiment of the invention with a florescent screen-based detection assembly.

The type of radiation detectors 20 can vary depending on the measurement's efficiency requirements. Various film can be used with or without an automatic swapping mechanism. In other embodiments, instead of using film to capture images, solid-state detector arrays (such as amorphous-silicon) or florescent screens coupled with a camera can be used. FIG. 4 shows the use of a florescent screen 21 coupled with a camera 75, where a mirror 70 is used to capture the resulting images with the camera 75 for analysis. In such embodiments, the use of solid-state detector arrays or florescent screens coupled with a camera allows efficient measurement and analysis of all node positions. With additional costs, an amorphous silicon panel can be used for direct digital measurement to simplify the mechanical configuration.

In the current embodiment, where the radiographic detector 20 is film, verification of beam alignment is accomplished by analyzing the field of the resulting radiographic image of the alignment fixture 15 for eccentricity. If the radiation beam 5 is perfectly aligned with the alignment center 14, and with the alignment fixture being a metallic ball, the resulting exposure on the film 20 will show a perfectly concentric circular radiation field.

This invention allows verification of all pre-calibrated radiation beam positions. The analysis obtained can be utilized to re-calibrate the beam (node) alignment either manually by entering beam correction data or automatically by digitally updating beam correction data.

In addition to the verification of beam alignment, by measuring the field width of 50% intensity (FWHM, or Field Width of Half Magnitude), the source-to-alignment center distance (SAD) can also be determined as described in patent application Ser. No. 12/006,629, Apparatus and Method for Robotic Radiosurgery Beam Geometry Quality Assurance, Wu, Xiaodong.

It is to be understood, that the subject invention described herein is not limited to the particular embodiments of the invention described herein, as variations of the particular embodiments may be made and still fall within the scope. It is also to be understood that the terminology employed is for the purpose of describing particular embodiments, and is not intended to be limiting.

It should be noted that the methods and apparatus described herein are not limited to use only with robotic radiosurgery treatment. In alternative embodiments, the methods and apparatus herein may be used in applications within other areas of the medical technology field as well as outside the medical technology field utilizing the application of radiation beams.

The contents of all patents, patent applications, published articles, books, reference manuals and abstracts cited herein are hereby incorporated by reference in their entirety to more fully describe the state of art to which the invention pertains.

As various changes can be made in the above-described subject matter without departing from the scope and the spirit of the invention, it is intended that all subject matter contained in the above description, shown in the accompanying drawings, or defined in the appended claims will be interpreted as descriptive and illustrative, and not in a limiting sense. Many modifications and variations of the present invention are possible in light of the above teachings. It is therefore to be understood that within the scope of the appended claims, the invention may be practiced otherwise than as specifically described.

Equivalents

Those skilled in the art will recognize, or be able to ascertain using no more than routine experimentation, many equivalents to the specific embodiments of the invention described herein. Such equivalents are intended to be encompassed by the claims.

What is claimed is:

1. A method for verifying radiation beam alignment, comprising:
   providing a LINAC having a radiographic image guidance system and having a laser light beam that corresponds to the central axis of the LINAC;
   providing a beam detection apparatus which is mounted on a gimbal assembly;
   providing a beam detection apparatus having:
      a housing generally shaped as a cube or rectangle; and
      an alignment fixture that is supported in the housing and centered on the common rotation center of the gimbal assembly; and
      a radiation detector to detect radiation emitted from the LINAC and positioned on one side of the housing; and
      an alignment mirror positioned on the opposite side of the housing from the radiation detector such that it is parallel to said radiation detector;
   using the LINAC's image guidance system, the alignment fixture is positioned at an alignment center or isocenter of the LINAC; and
   selecting a node and positioning the LINAC at that node; and
   activating the laser light beam;
   adjusting the beam detection apparatus which is mounted on the gimbal assembly such that the alignment mirror is perpendicular to the laser light beam by locating the reflection of the laser light beam along the axis of the inbound laser light beam;
   delivering an amount of radiation from the LINAC to the alignment fixture with a collimator affixed on the LINAC;
   detecting or capturing a radiographic image of the alignment fixture on the radiation detector of the beam detection apparatus;
   analyzing the resulting image of the alignment fixture for eccentricity; and
   adjusting the node position to eliminate eccentricity.

2. The method of claim 1, wherein the radiographic image of the alignment fixture is captured using solid-state detector arrays.

3. The method of claim 1, wherein the radiographic image of the alignment fixture is captured using fluorescent screens coupled with a camera.

4. An apparatus for detecting and verifying radiation beam alignment, comprising:
   a housing generally shaped as a cube or rectangle; and
   an alignment fixture that is supported in the housing and centered on the common rotation center of a gimbal assembly and is made of radio-opaque material in a symmetric geometric shape; and
   a radiation detector positioned on one side of the housing; and
   an alignment mirror positioned on the opposite side of the housing from the radiation detector such that it is parallel to the radiation detector; and
   the housing is attached to the gimbal assembly on the two opposing sides of the housing that do not support the radiation detector or alignment mirror.

5. The apparatus in claim 4, wherein the gimbal assembly is motorized and controlled by computer and gimbal position is automatically provided to the computer, and said computer is integrated into a LINAC's image guidance system.

6. The apparatus in claim 4 wherein the alignment fixture that is supported in the housing and centered on the common rotation center of the gimbal assembly is made of steel.

7. An apparatus for detecting and verifying radiation beam alignment comprising:
   a housing generally shaped as a cube or rectangle; and
   an alignment fixture that is supported in the housing and centered on the common rotation center of a gimbal assembly and is an array of radio-opaque markers; and
   a radiation detector positioned on one side of the housing; and
   an alignment mirror positioned on the opposite side of the housing from the radiation detector such that it is parallel to the radiation detector; and
   the housing is attached to the gimbal assembly on the two opposing sides of the housing that do not support the radiation detector or alignment mirror.

8. The apparatus in claim 7, wherein the gimbal assembly is motorized and controlled by computer, and gimbal position is automatically provided to the computer, and said computer is integrated into a LINAC's image guidance system.

* * * * *